(12) United States Patent
Fu et al.

(10) Patent No.: US 8,554,517 B2
(45) Date of Patent: Oct. 8, 2013

(54) PHYSIOLOGICAL SIGNAL QUALITY CLASSIFICATION FOR AMBULATORY MONITORING

(75) Inventors: Yongji Fu, Vancouver, WA (US); Te-Chung Isaac Yang, Aliso Viejo, CA (US)

(73) Assignee: Sharp Laboratories of America, Inc., Camas, WA (US)

( * ) Notice: Subject to any disclaimer, the term of this patent is extended or adjusted under 35 U.S.C. 154(b) by 495 days.

(21) Appl. No.: 12/660,458

(22) Filed: Feb. 25, 2010

(65) Prior Publication Data

US 2011/0208009 A1  Aug. 25, 2011

(51) Int. Cl.
*G06F 19/00* (2011.01)
*H03F 1/26* (2006.01)

(52) U.S. Cl.
USPC .......................... 702/189; 600/524; 702/190

(58) Field of Classification Search
USPC ................. 600/300, 301, 508, 509, 524, 529, 600/544
See application file for complete search history.

(56) References Cited

U.S. PATENT DOCUMENTS

| 5,305,202 A | 4/1994 | Gallant et al. ................ 600/524 |
| 6,370,423 B1 | 4/2002 | Guerrero et al. ............. 600/513 |
| 7,207,948 B2 | 4/2007 | Coyle ........................... 600/538 |
| 7,477,144 B2 | 1/2009 | Albert .......................... 340/521 |
| 2004/0133244 A1* | 7/2004 | Vaisnys et al. .................... 607/5 |
| 2006/0233390 A1* | 10/2006 | Causevic et al. ............. 381/94.1 |
| 2006/0276702 A1* | 12/2006 | McGinnis ..................... 600/372 |
| 2007/0149862 A1 | 6/2007 | Pipke | |
| 2008/0162088 A1* | 7/2008 | DeVaul et al. ................ 702/190 |
| 2008/0183082 A1 | 7/2008 | Farringdon et al. ........... 600/481 |

FOREIGN PATENT DOCUMENTS

| EP | 0951866 | 10/1999 |
| WO | WO2007/052108 | 5/2007 |

OTHER PUBLICATIONS

J. Martinek et al., "Distinction Between Voluntary Cough Sound and Speech in Volunteers by Spectral and Complexity Analysis," 2008, 59 J. Physiology and Pharmacology, Supp. 6, 433-40 < < http://www.jpp.krakow.pl/journal/archive/1208_s6/articles/39_article.html > >.

J. Gnitecki et al., "Separating Heart Sounds from Lung Sounds," IEEE Eng. Med. Bio. Magazine, Jan./Feb. 2007, 20-29.

* cited by examiner

*Primary Examiner* — John H Le
(74) *Attorney, Agent, or Firm* — Scot A. Reader

(57) ABSTRACT

Physiological signal quality classification methods and systems for ambulatory monitoring. Physiological signals are classified as good, noisy or weak based on signal properties. Once classified, signals are processed differently depending on their classification For example, for a good signal, physiological data may be extracted from the signal and displayed to a person being monitored. For a noisy signal, a noisy signal notification may be displayed to the person in lieu of extracted physiological data. For a weak signal, a weak signal notification may be displayed to the person in lieu of extracted physiological data. Moreover, a noisy or weak signal notification displayed to a person being monitored may be accompanied by a corrective action recommendation, such as "move to quieter environment" for a noisy signal or "check body placement of sensor" for a weak signal.

8 Claims, 8 Drawing Sheets

PHYSIOLOGICAL SIGNAL QUALITY CLASSIFICATION FOR AMBULATORY MONITORING

BACKGROUND OF THE INVENTION

The present invention relates to ambulatory monitoring and, more particularly, to physiological signal quality classification methods and systems designed to improve ambulatory monitoring.

Ambulatory monitoring of the physiological state of people who suffer from chronic diseases is an important aspect of chronic disease management. By way of example, ambulatory monitoring is in widespread use managing chronic diseases such as asthma and in elder care.

Ambulatory monitoring is often performed using wearable devices that acquire and analyze physiological signals, such as heart and lung sounds, as people go about their daily lives. These signals are not always reliable. For example, a signal may be too noisy when a person speaks, or is in motion, or is in an environment with high background noise. Moreover, a signal may be too weak when a person does not place a sensor of the device at the proper body location or when an air chamber of the sensor is not fully sealed. When a signal is too noisy or too weak, confidence in physiological data extracted from the signal, such as the patient's heart rate, may be very low.

Physiological data extracted from an unreliable physiological signal can have serious adverse consequences on patient health. For example, such physiological data can lead a patient or his or her clinician to improperly interpret the patient's physiological state and cause the patient to undergo treatment that is not medically indicated or forego treatment that is medically indicated.

SUMMARY OF THE INVENTION

The present invention provides physiological signal quality classification methods and systems designed to improve ambulatory monitoring. The present invention, generally speaking, classifies physiological signals as good, noisy or weak based on signal properties. Once classified, signals are processed differently depending on their classification to avoid extracting unreliable physiological data and to induce action to improve signal quality. For example, where a signal is good, physiological data may be extracted from the signal and displayed to a person being monitored. Where a signal is noisy, a noisy signal notification may be displayed to the person in lieu of extracted physiological data. Where a signal is weak, a weak signal notification may be displayed to the person in lieu of extracted physiological data. Moreover, a noisy or weak signal notification displayed to a person being monitored may be accompanied by a corrective action recommendation, such as "move to quieter environment" for a noisy signal or "check body placement of sensor" for a weak signal.

In one aspect of the invention, a physiological signal processing method for an ambulatory monitoring system comprises the steps of comparing by the system one or more properties of a physiological signal with one or more distinguishing properties of good, noisy and weak signals; classifying by the system the signal as one of good, noisy or weak based on the comparison; and processing by the system the signal in accordance with the classification.

In some embodiments, the method further comprises the steps of extracting by the system an envelope for the signal; and generating by the system using the envelope an autocorrelation result for the signal, wherein the comparison is between one or more properties of the autocorrelation result and one or more distinguishing properties of good, noisy and weak signals.

In some embodiments, the distinguishing properties comprise central peak width.

In some embodiments, the distinguishing properties comprise non-central peak width.

In some embodiments, the classifying step comprises classifying the signal as good based at least in part on a determination that a central peak of the signal has a width between a low central peak width threshold and a high central peak width threshold and a determination that a non-central peak of the signal has a width above a non-central peak width threshold.

In some embodiments, the classifying step comprises classifying the signal as noisy based at least in part on a determination that a central peak of the signal has a width above a high central peak width threshold.

In some embodiments, the classifying step comprises classifying the signal as weak based at least in part on a determination that a central peak of the signal has a width below a low central peak width threshold.

In some embodiments, the classifying step comprises classifying the signal as weak based at least in part on a determination that no non-central peak of the signal has a width above a non-central peak width threshold.

In some embodiments, the processing step comprises extracting physiological data from the signal in response to classifying the signal as good, and outputting the physiological data.

In some embodiments, the processing step comprises generating a noisy signal notification in response to classifying the signal as noisy, and outputting the noisy signal notification.

In some embodiments, the processing step comprises generating a weak signal notification in response to classifying the signal as weak, and outputting the weak signal notification.

In another aspect of the invention, an ambulatory monitoring system comprises a transducer; and a signal processor communicatively coupled with the transducer, wherein under control of the signal processor the system compares one or more properties of a physiological signal detected by the transducer with one or more distinguishing properties of good, noisy and weak signals, classifies the signal as one of good, noisy or weak based on the comparison, and processes the signal in accordance with the classification.

In some embodiments, under control of the signal processor the system extracts an envelope for the signal, and generates using the envelope an autocorrelation result for the signal, wherein the comparison is between one or more properties of the autocorrelation result and one or more distinguishing properties of good, noisy and weak signals.

In some embodiments, under control of the signal processor the system classifies the signal as good based at least in part on a determination that a central peak of the signal has a width between a low central peak width threshold and a high central peak width threshold and a determination that a non-central peak of the signal has a width above a non-central peak width threshold.

In some embodiments, under control of the signal processor the system classifies the signal as noisy based at least in part on a determination that a central peak of the signal has a width above a high central peak width threshold.

In some embodiments, under control of the signal processor the system classifies the signal as weak based at least in part on a determination that a central peak of the signal has a width below a low central peak width threshold.

In some embodiments, under control of the signal processor the system classifies the signal as weak based at least in part on a determination that no non-central peak of the signal has a width above a non-central peak width threshold.

In yet another aspect of the invention, an ambulatory monitoring system comprises a transducer; and a signal processor communicatively coupled with the transducer, wherein under control of the signal processor the system compares signal peak widths of an autocorrelation result of a physiological signal generated by the transducer with predetermined signal peak width thresholds distinguishing a plurality of signal types, classifies the signal into one of the signal types based on the comparison, and processes the signal in accordance with the classification.

In some embodiments, the plurality of signal types comprise at least two of good, noisy and weak.

In some embodiments, the signal peak widths of the autocorrelation result comprise a central peak width and a non-central peak width.

In some embodiments, under control of the signal processor the system classifies the signal as good based at least in part on a determination that a central peak width of the signal is between a low central peak width threshold and a high central peak width threshold and a determination that a non-central peak width of the signal is above a non-central peak width threshold.

In some embodiments, under control of the signal processor the system classifies the signal as noisy based at least in part on a determination that a central peak width of the signal is above a high central peak width threshold.

In some embodiments, under control of the signal processor the system classifies the signal as weak based at least in part on a determination that no non-central peak width of the signal is above a non-central peak width threshold.

These and other aspects of the invention will be better understood by reference to the following detailed description taken in conjunction with the drawings that are briefly described below. Of course, the invention is defined by the appended claims.

DETAILED DESCRIPTION OF A PREFERRED EMBODIMENT

Figure 1:
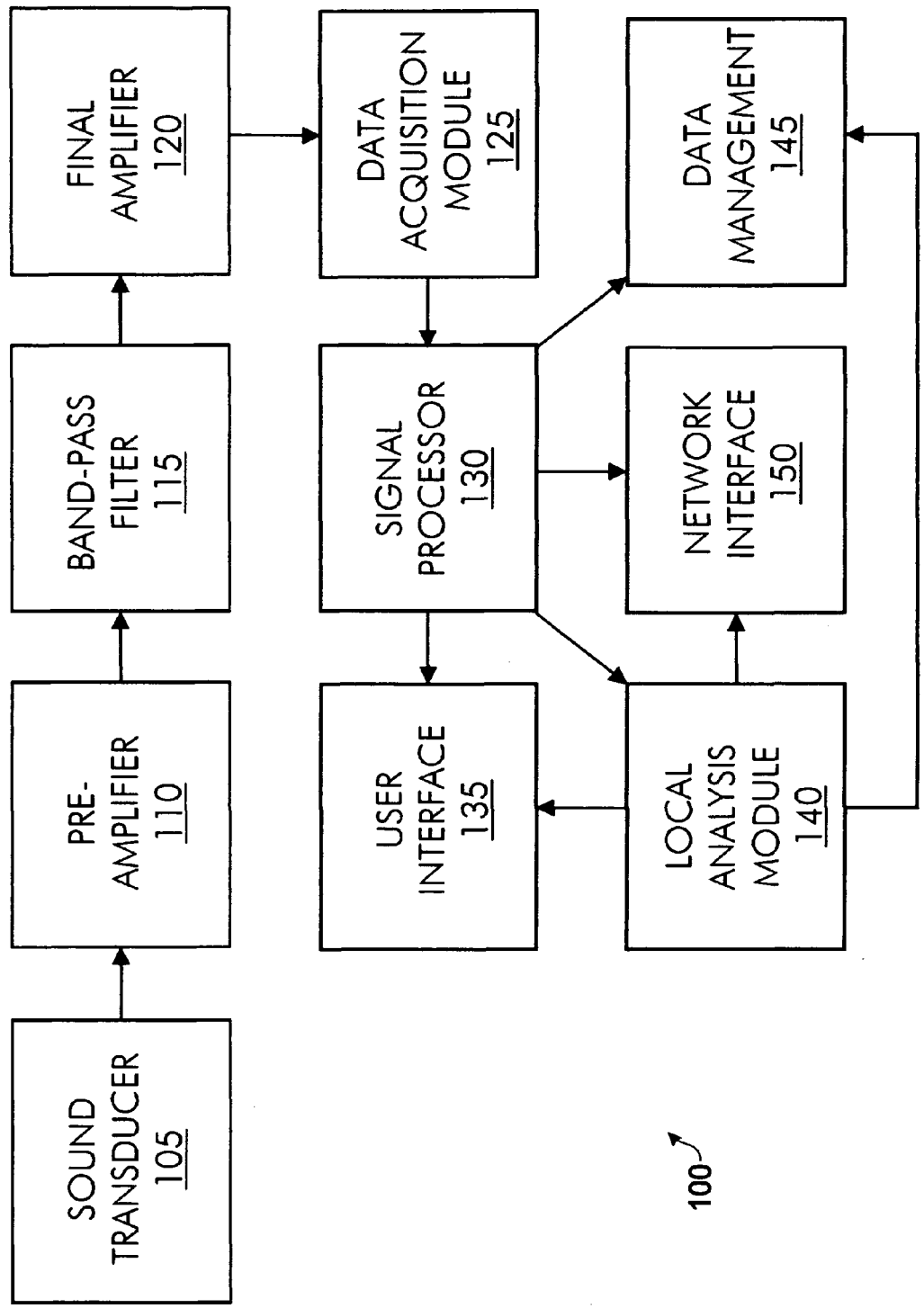
FIG. 1 shows an ambulatory monitoring system in some embodiments of the invention.

FIG. 1 shows an ambulatory monitoring system 100 in some embodiments of the invention. System 100 includes a sound transducer 105 positioned on the body of a human subject being monitored. By way of example, transducer 105 may be positioned at a patient's trachea, chest or back. Transducer 105 is communicatively coupled in series with a pre-amplifier 110, band-pass filter 115, amplifier 120 and data acquisition module 125. Data acquisition module 125 transmits acoustic physiological signals generated from sounds detected by transducer 105, as modified by amplifiers 110, 120 and filter 115, to a signal processor 130. Signal processor 130 processes the signals and outputs information generated from the signals to a user interface 135, a local analysis module 140, a data management element 145 and/or a network interface 150. The elements shown in FIG. 1, may be collocated or located remotely from one another. Adjacent elements shown in FIG. 1 may be communicatively coupled via wired or wireless links. In some embodiments, elements 105-150 are part of a wearable device that monitors a person's physiological state in real-time as the person performs daily activities.

Transducer 105 detects physiological sounds at a detection point, such as a person's trachea, chest or back. Transducer 105 in some embodiments is an omni-directional piezo ceramic microphone. A microphone marketed by Knowles Acoustics as part BL-21785 may be used by way of example. Transducer 105 transmits acoustic physiological signals in the form of electrical signals generated from detected physiological sounds to pre-amplifier 110 as analog voltages on the order of 10-200 mV.

Pre-amplifier 110 provides impendence match for acoustic physiological signals received from transducer 105 and amplifies the signals to a level appropriate for filter stage that follows. A pre-amplifier marketed by Presonus Audio Electronics as TubePre Single Channel Microphone Preamp with VU (Volume Unit) Meter may be used by way of example.

Band-pass filter 115 is an analog filter that applies a high-pass cutoff frequency at 80 Hz and a low-pass cutoff frequency at 2 KHz to acoustic physiological signals received from pre-amplifier 110 to reduce noise, for example, muscle and contact noise.

Final amplifier 120 amplifies the acoustic physiological signals received from filter 115 to the range of +/−1 V.

Data acquisition module 125 performs A/D conversion on the acoustic physiological signals received from amplifier 120 and transmits the signals to signal processor 130 for analysis. Data acquisition module 125 may also provide automatic gain control to adjust the amplitude of the signals provided to signal processor 130 without impacting on signal-to-noise ratio.

Signal processor 130 is a microprocessor having software executable thereon for performing signal processing on acoustic physiological signals received from data acquisition module 125. Signal processing includes classifying the acoustic physiological signals as one of normal, noisy or weak based on signal properties. Once classified, signals are processed differently depending on their classification to avoid extracting unreliable physiological data and to induce action to improve signal quality if necessary. For example, for a signal classified as good, physiological data may be extracted from the signal and sent to user interface 135 whereon the data are displayed, sent to local analysis module 140 whereon the data are subjected to higher level clinical processing, sent to data management element 145 whereon the data are logged, and/or sent to network interface 150 for transmission to a remote analysis module or remote clinician display. For a signal classified as noisy, a noisy signal notification may be sent to elements 135, 140, 145 and/or 150 in lieu of physiological data. For a signal classified as weak, a weak signal notification may be sent to elements 135, 140, 145 and/or 150 in lieu of physiological data. Moreover, a noisy or weak signal notification sent to and displayed on user interface 135 and/or a remote clinician display may be accompanied by a corrective action recommendation, such as "move to quieter environment" for a noisy signal or "check body placement of sensor" for a weak signal, giving guidance on how to improve signal quality.

An acoustic physiological signal processing method performed in ambulatory monitoring system 100 under control of signal processor 130 will now be described by reference to the flow diagrams of FIGS. 11 and 13, taken in conjunction with the charts of FIGS. 2-10 and 12. In the illustrated example, the goal of ambulatory monitoring is to provide real-time heart rate data based on heart sounds detected at the trachea. However, it bears noting that the method can be applied to achieve other ambulatory monitoring goals, such as providing real-time respiratory rate data based on lung sounds, and can provide such data based on detection elsewhere on the patient's body, such as the patient's chest or back. Moreover, while an ambulatory monitoring system that uses a sound transducer is described herein, an ambulatory monitoring system that uses another type of transducer, such as an electrical (e.g. electrocardiogram) or optical transducer, may be used in other embodiments.

Figure 2:
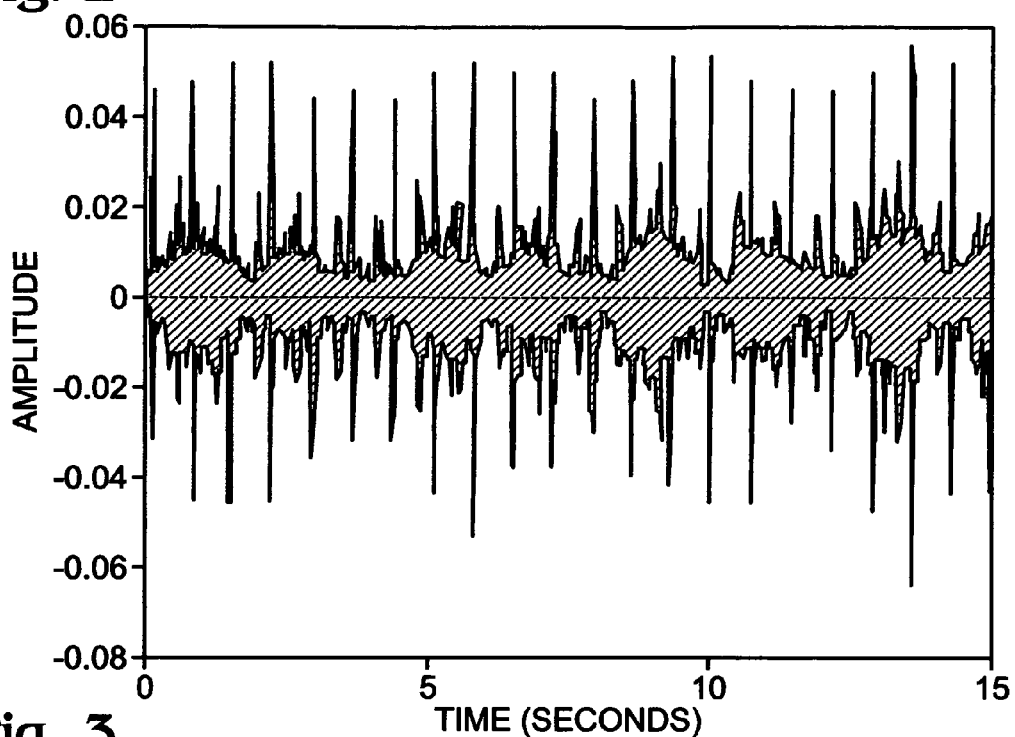
FIG. 2 shows a good acoustic physiological signal received by a signal processor in some embodiments of the invention.

In Step 1105, an acoustic physiological signal is acquired by signal processor 130 from data acquisition module 125. FIG. 2 shows a good tracheal acoustic physiological signal received by signal processor 130 from data acquisition module 125. The illustrated signal was acquired over 15 seconds at a sample frequency of 3.2 KHz. The X-axis is time in seconds and the Y-axis is signal amplitude. The signal includes several body sounds (heartbeat, respiratory sounds, etc.) intermingled with noise from different sources. Heartbeat is the body sound of interest since the stated ambulatory monitoring goal in the present example is to provide real-time heart rate data.

Figure 5:
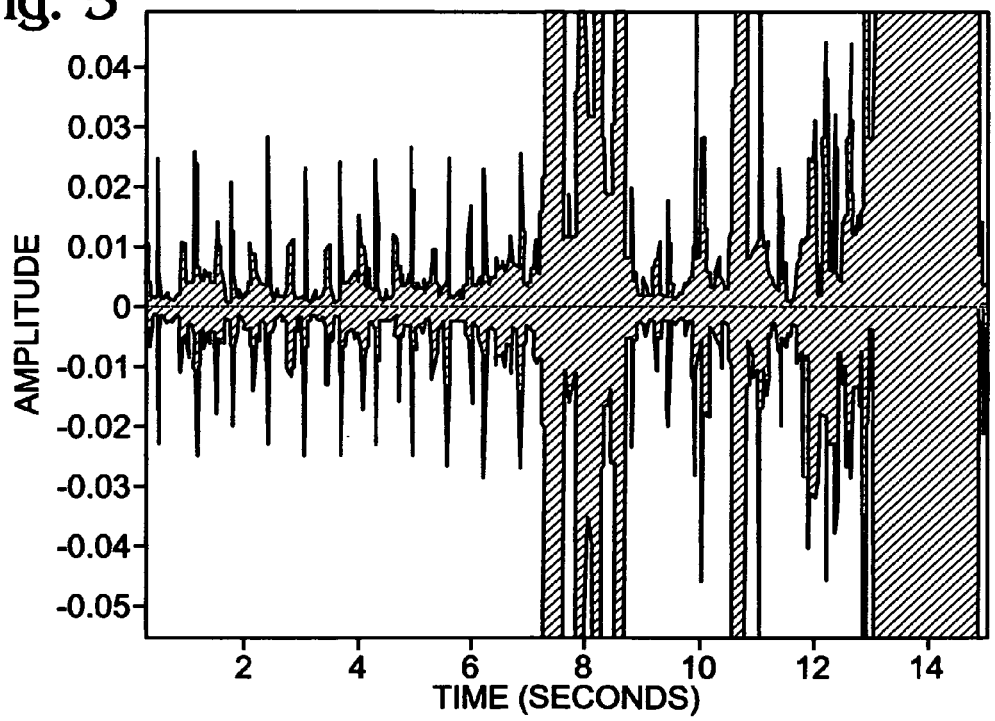
FIG. 5 shows a noisy acoustic physiological signal received by a signal processor in some embodiments of the invention.

FIG. 5 shows a noisy tracheal acoustic physiological signal received by signal processor 130 from data acquisition module 125. The illustrated signal was also acquired over 15 seconds at a sample frequency of 3.2 KHz and the X-axis is again time in seconds and the Y-axis is signal amplitude. The signal again includes several body sounds and noise from different sources. However, the signal shown in FIG. 5 is disrupted by strong noise in the latter part of the sampling window (e.g. seconds 7 to 15), making it difficult to isolate body sounds, such as heartbeat, in the signal. The strong noise may have resulted from, for example, excessive background noise in the environment of the person being monitored.

Figure 8:
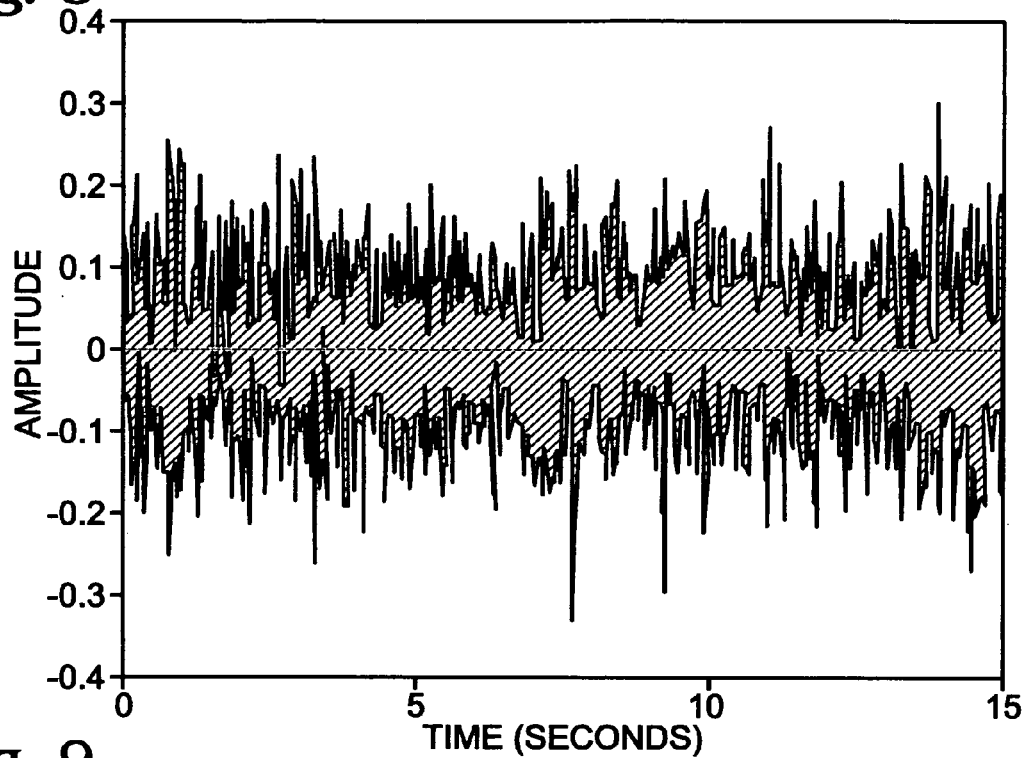
FIG. 8 shows a weak acoustic physiological signal received by a signal processor in some embodiments of the invention.

FIG. 8 shows a weak tracheal acoustic physiological signal received by signal processor 130 from data acquisition module 125. The illustrated signal was also acquired over 15 seconds at a sample frequency of 3.2 KHz. The X-axis is again time in seconds and the Y-axis is signal amplitude. The signal again includes several body sounds and noise from different sources. However, the body sounds exhibited in the signal shown in FIG. 8 are weak throughout the sampling window, making them difficult to isolate. Weakness of body sounds may have been attributable to, for example, improper placement of sound transducer 105 on the body of the person being monitored.

In Step 1110, a band-pass filter is applied to the acoustic physiological signal to attempt to isolate body sounds of interest. As heart sounds are typically found within the 20 to 120 Hz frequency range, a band-pass filter having a cutoff frequency of 20 Hz at the low end and 120 Hz at the high end is applied to the signal to isolate heartbeat.

Figure 3:
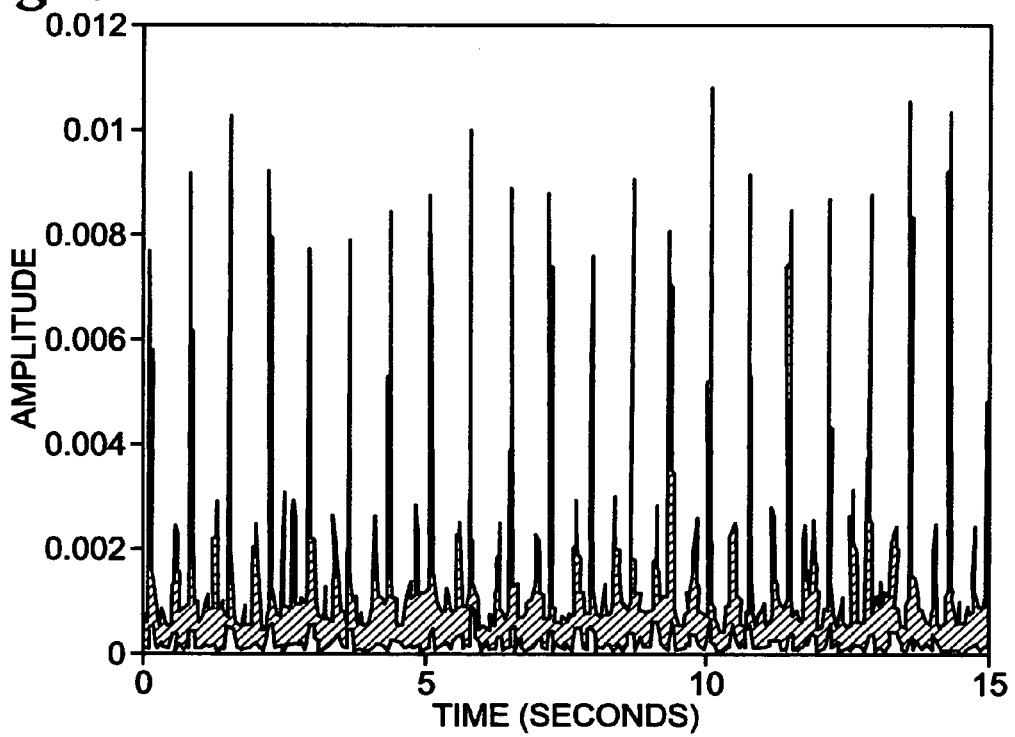
FIG. 3 shows an envelope of the signal of FIG. 2.

In Step 1115, a signal envelope is extracted from the acoustic physiological signal to remove noise and improve signal quality. The signal envelope can be extracted in several ways. For example, a standard deviation can be calculated in a short window and the window can be slid to detect the envelope. FIG. 3 shows an extracted envelope of the good signal of FIG. 2. The periodic heartbeat is clearly expressed in the signal envelope, enabling heart rate data to be reliably extracted.

Figure 6:
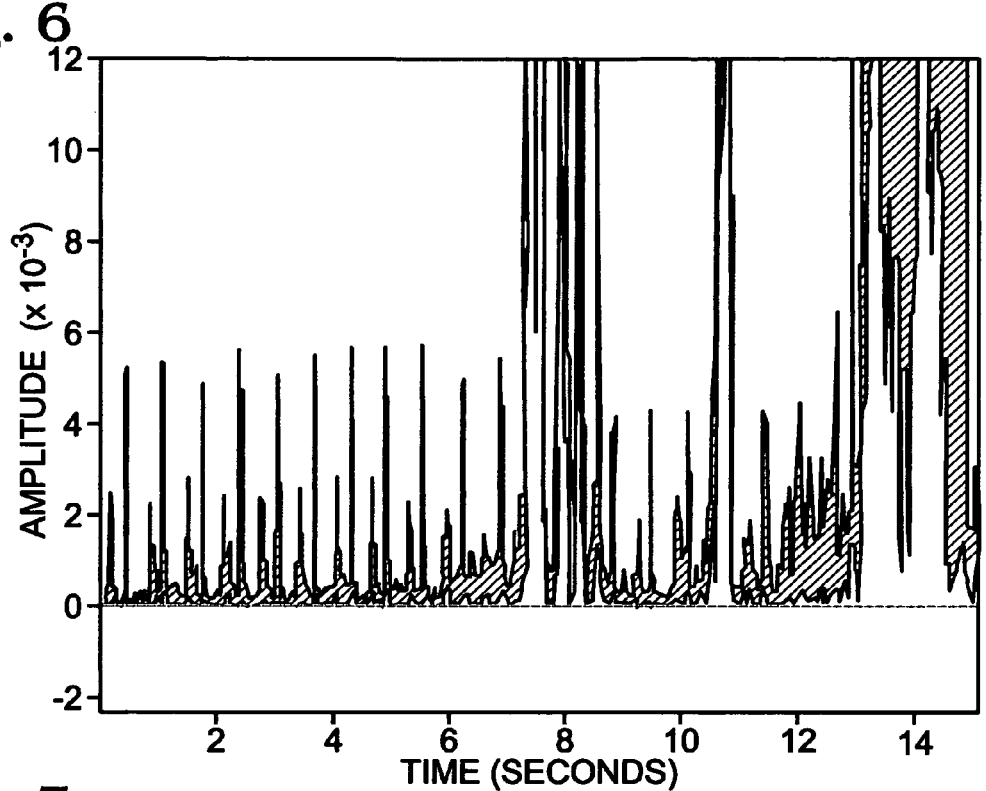
FIG. 6 shows an envelope of the signal of FIG. 5.

FIG. 6 shows an extracted envelope of the noisy signal of FIG. 5. The periodic heartbeat is not clearly expressed in the signal envelope due to noise.

Figure 9:
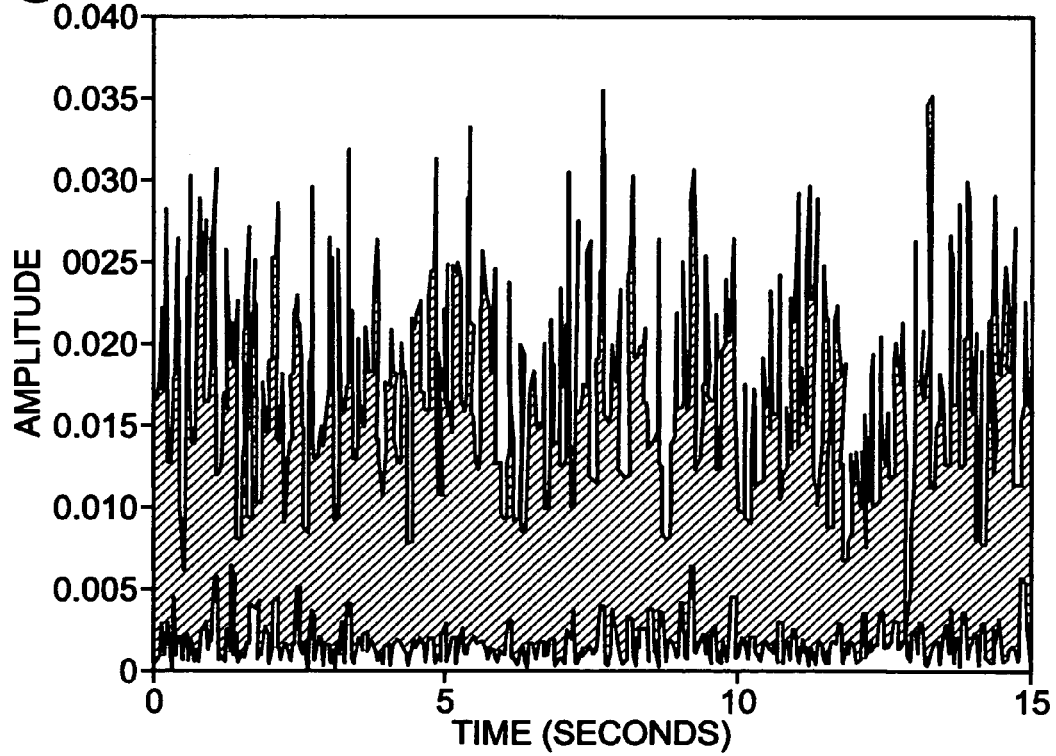
FIG. 9 shows an envelope of the signal of FIG. 8.

FIG. 9 shows an extracted envelope of the weak signal of FIG. 8. The periodic heartbeat is not clearly expressed in the signal envelope due to weak detection of heartbeat.

Figure 4:
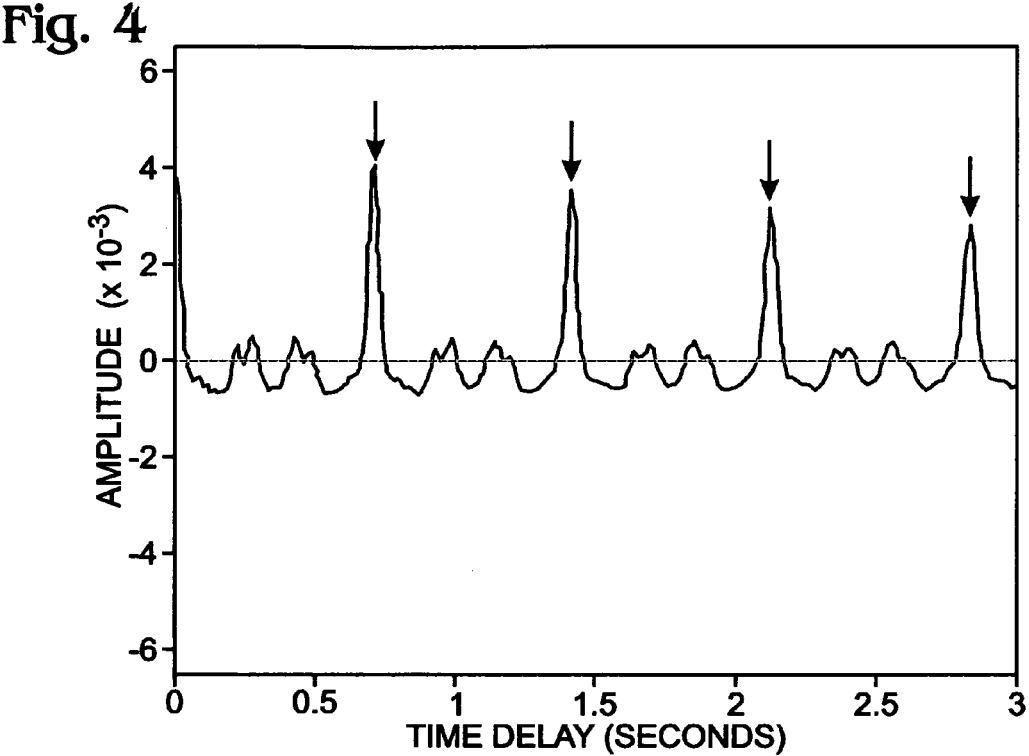
FIG. 4 shows an autocorrelation curve of the envelope of FIG. 3.

In Step 1120, an autocorrelation function is applied to the envelope to identify fundamental periodicity in the acoustic physiological signal. FIG. 4 shows the positive-half time delay of an autocorrelation result generated from the good signal envelope of FIG. 3. The autocorrelation result is characterized by significant signal peaks (at locations indicated by arrows) including a central peak centered at zero time delay (t=0) and non-central peaks centered at non-zero time delay, representing a heartbeat from which heart rate data can be reliably extracted. More particularly, significant peaks occur about every 0.7 seconds, which indicates a heart rate of roughly 85 beats per minute (60/0.7=85.7).

Figure 7:
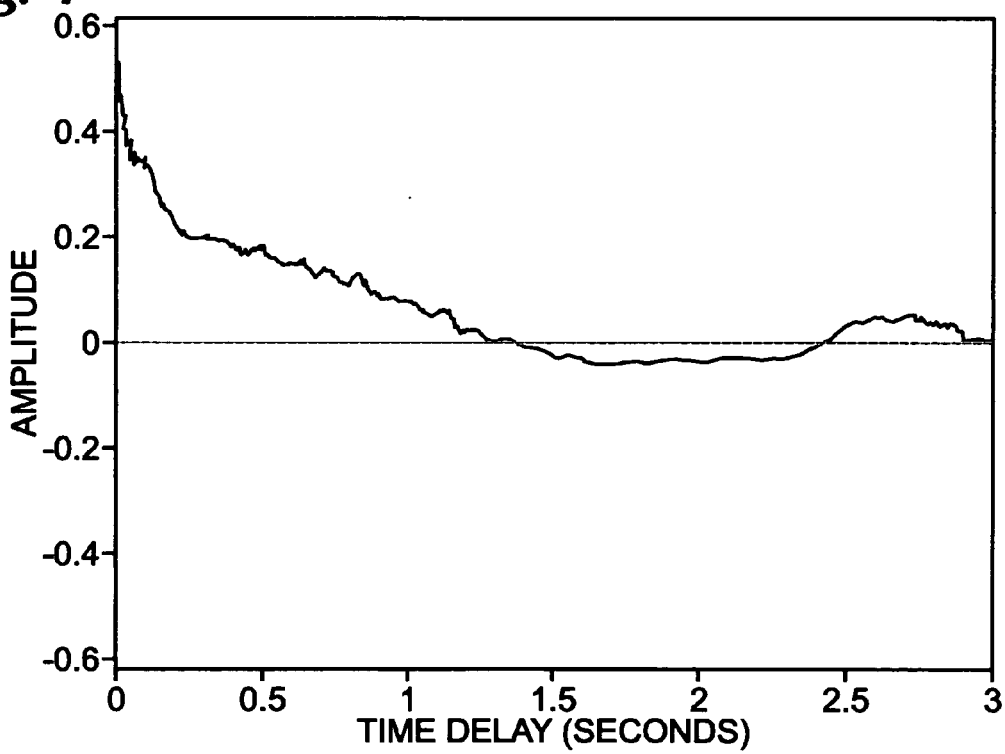
FIG. 7 shows an autocorrelation curve of the envelope of FIG. 6.

FIG. 7 shows the positive-half time delay of an autocorrelation result generated from the noisy signal envelope of FIG. 6. The autocorrelation result is characterized by central peak having a large width, reflecting a signal whose periodic energy (e.g. heartbeat) is largely subsumed in higher energy noise. This noise prevents heart rate data from being reliably extracted from the signal.

Figure 10:
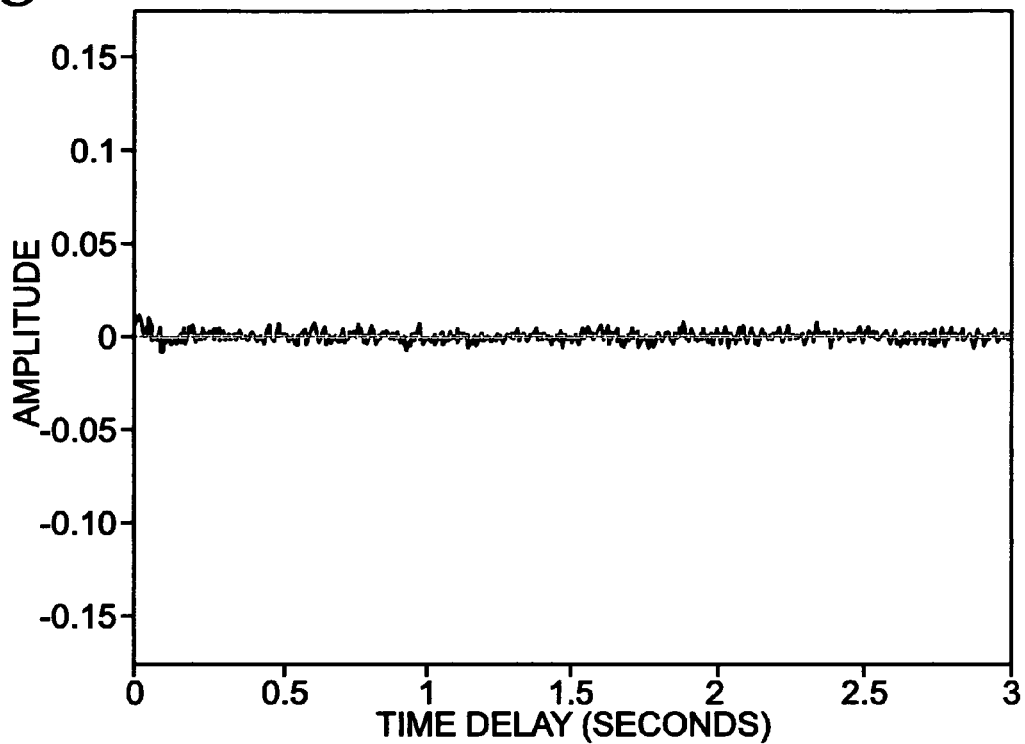
FIG. 10 shows an autocorrelation curve of the envelope of FIG. 9.
Figure 11:
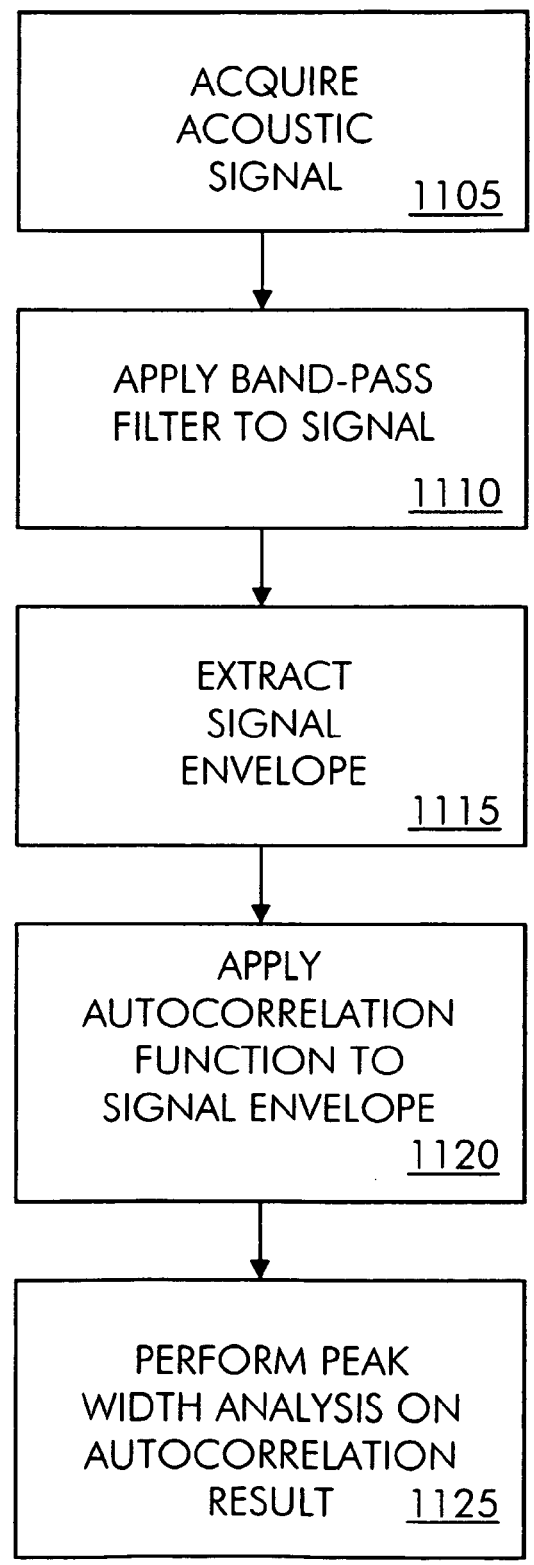
FIG. 11 shows an acoustic physiological signal processing method in some embodiments of the invention.

FIG. 10 shows the positive-half time delay of an autocorrelation result generated from the weak signal envelope of FIG. 9. The autocorrelation result is characterized by the absence of any significant signal peak, reflecting a signal whose periodic energy (e.g. heartbeat) is largely nonexistent due to weak detection. This weak detection prevents heart rate data from being reliably extracted from the signal.

In Step 1125, a peak width analysis is performed on the autocorrelation result to classify the acoustic physiological signal as one of good, noisy or weak. The analysis compares peak width properties of the signal with distinguishing peak width properties of good, noisy and weak signals, and classifies the signal based on the comparison.

Figure 12:
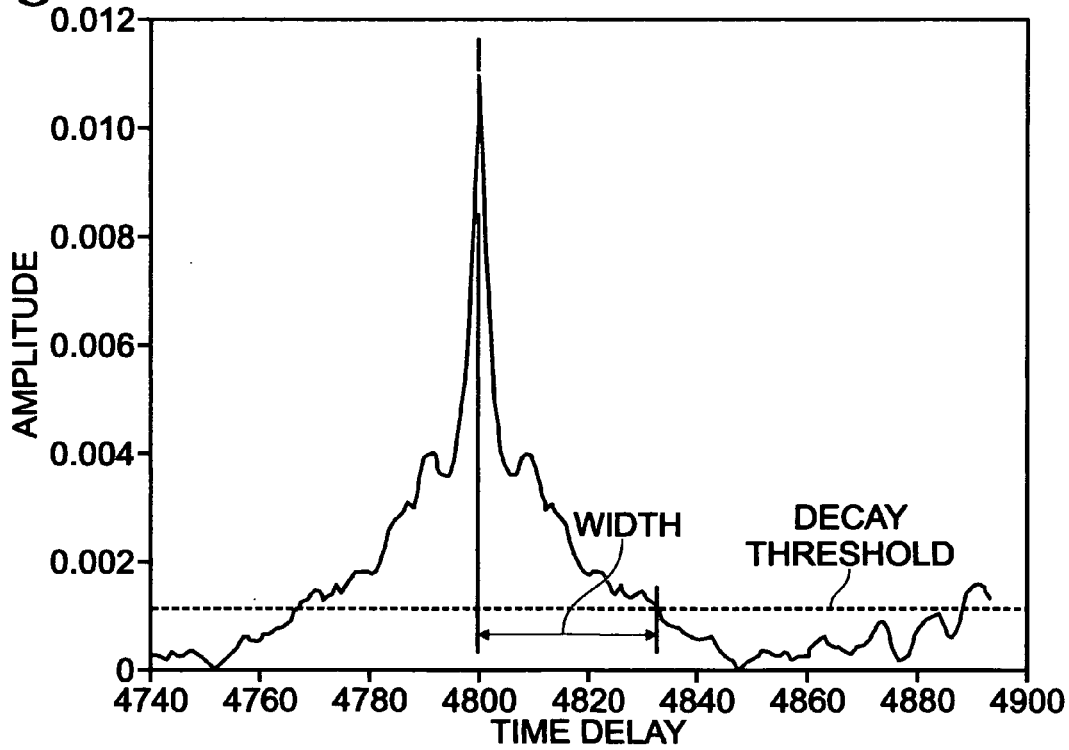
FIG. 12 shows a peak having a measured width in some embodiments of the invention.

Turning to FIG. 12, an exemplary peak having a measured width for application in classification of the acoustic physiological signal using peak width analysis is shown. In the illustrated example, the peak width is measured as a half-width in the positive time delay direction from peak amplitude to a peak decay threshold at 10 percent of peak amplitude. Naturally, in other embodiments peak width may be measured as a full width, may be measured in the negative time delay direction and/or may be measured from peak amplitude to a peak delay threshold at other than 10 percent of peak amplitude.

Figure 13:
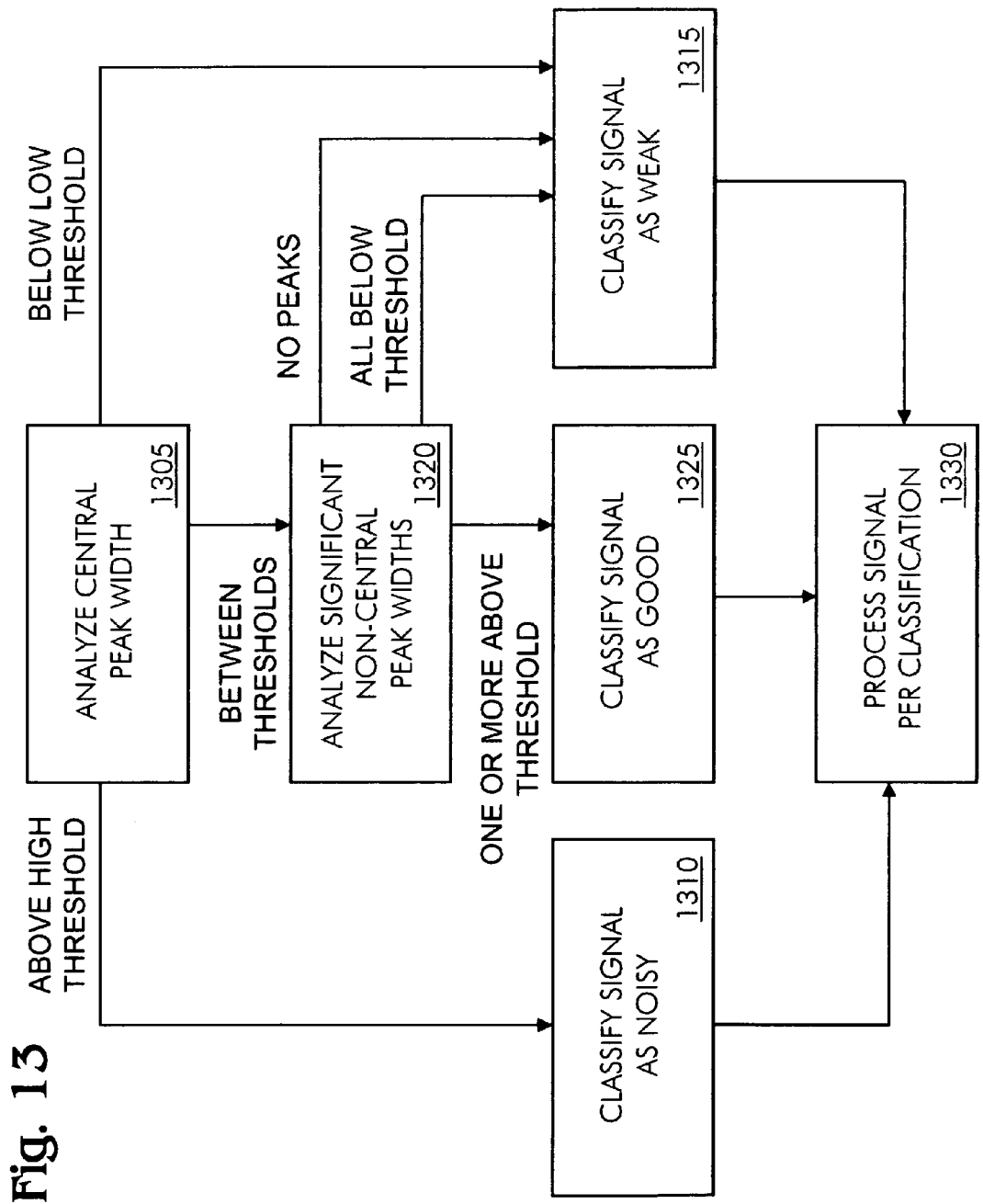
FIG. 13 shows signal classification steps of an acoustic physiological signal processing method in some embodiments of the invention.

FIG. 13 shows signal classification steps of an acoustic physiological signal processing method in some embodiments of the invention. Initially, the central peak of an autocorrelation result obtained in Step 1120 is normalized to one to ensure proper analysis. Then, in Step 1305, the width of the central peak is compared with central peak width thresholds. If the central peak width is above a high central peak width threshold, the signal is classified as noisy at Step 1310. If the central peak is below a low central peak width threshold, the signal is classified as weak at Step 1315. If the central peak width is between the high and low central peak width thresholds, further analysis is required. In that event, significant non-central peaks (e.g. peaks centered at positive time delay), if any, are identified and their width is analyzed at Step 1320. If there are no significant non-central peaks, the signal is classified as weak at Step 1320. If there are significant non-central peaks, they are compared with a non-central peak width threshold. If none of the significant non-central peaks has a width above the non-central peak width threshold, the signal is classified as weak at Step 1320. If, however, at least one of the significant non-central peaks has a width above the non-central peak width threshold, the signal is classified as good at Step 1325. The flow then proceeds, regardless of how the signal is classified, to Step 1330 where the signal is processed in accordance with its assigned classification.

If the signal has been classified as good, under control of signal processor 130 physiological data (e.g. heart rate) are extracted from the signal and transmitted to user interface 135 whereon the physiological data are displayed to the person being monitored, transmitted to local analysis module 140 whereon the data are subjected to higher level clinical processing, transmitted to data management element 145 whereon the data are logged, and/or transmitted to network interface 150 for further transmission to a remote analysis module or remote clinician display. If the signal has been classified as noisy, physiological data are not extracted from the signal and under control of signal processor 130 a noisy signal notification is instead outputted to/on one or more of elements 135, 140, 145, 150. If the signal has been classified as weak, physiological data are not extracted from the signal and under control of signal processor 130 a weak signal notification is instead outputted to/on one or more of elements 135, 140, 145, 150. A corrective action recommendation appropriate for noisy signals may accompany a noisy signal notification, and a corrective action recommendation appropriate for weak signals may accompany a weak signal notification, to prompt action to improve signal quality.

Techniques for measuring the peak width of the signal and values assigned as peak width thresholds will vary with system requirements and monitored physiological parameters. In some embodiments where the monitored parameter is heart rate, the peak width of the signal may be measured as a half-width in the positive time delay direction from a peak amplitude to a peak decay threshold at 10 percent of peak amplitude, and may be compared with peak width thresholds assigned the following values:

High central peak width threshold=0.1 seconds
Low central peak width threshold=0.0125 seconds
Non-central peak width threshold=0.125 seconds Additionally, in these embodiments, a non-central peak may be deemed significant if it has a peak amplitude of at least 10 percent of the peak amplitude of the central peak.

It will be appreciated by those of ordinary skill in the art that the invention can be embodied in other specific forms without departing from the spirit or essential character hereof. The present description is therefore considered in all respects to be illustrative and not restrictive. The scope of the invention is indicated by the appended claims, and all changes that come within the meaning and range of equivalents thereof are intended to be embraced therein.

What is claimed is:

1. A physiological signal processing method for an ambulatory monitoring system, comprising the steps of:
   comparing by the ambulatory monitoring system peak width properties of physiological signals with distinguishing peak width properties of good, noisy and weak signals;
   classifying by the ambulatory monitoring system at least one of the physiological signals as good based on at least one of the comparisons; and
   processing by the ambulatory monitoring system the at least one physiological signal in accordance with the classification, wherein the at least one physiological signal is classified as good in response to a determination that a central peak of the at least one physiological signal has a width between a low central peak width threshold and a high central peak width threshold and a determination that a non-central peak of the at least one physiological signal has a width above a non-central peak width threshold, and wherein physiological data are extracted from the at least one physiological signal and outputted in response to classifying the at least one physiological signal as good.

2. The method of claim 1, further comprising the steps of:
   extracting by the ambulatory monitoring system envelopes for the physiological signals; and
   generating by the ambulatory monitoring system using the envelopes autocorrelation results for the physiological signals, wherein the comparisons are between peak width properties of the autocorrelation results and distinguishing peak width properties of good, noisy and weak signals.

3. The method of claim 1, wherein the physiological data comprise heart data.

4. The method of claim 1, wherein the physiological data comprise respiration data.

5. The method of claim 1, wherein the physiological data are outputted to a user interface whereon the physiological data are displayed.

6. The method of claim 1, wherein the physiological data are outputted to a local analysis module whereon the physiological data are subjected to higher level clinical processing.

7. The method of claim 1, wherein the physiological data are outputted to a data management element whereon the physiological data are logged.

8. The method of claim 1, wherein the physiological data are outputted to a network interface wherefrom the physiological data are transmitted remotely.

* * * * *